(12) United States Patent
Akerstrom et al.

(10) Patent No.: US 10,023,833 B2
(45) Date of Patent: Jul. 17, 2018

(54) TEMPERATURE SENSOR MEANS AND A BIOREACTOR SYSTEM COMPRISING A TEMPERATURE SENSOR MEANS

(71) Applicant: GE Healthcare Bio-Sciences AB, Uppsala (SE)

(72) Inventors: Patrik Akerstrom, Uppsala (SE); Hakan Wahlnas, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

(21) Appl. No.: 14/899,167

(22) PCT Filed: Jun. 16, 2014

(86) PCT No.: PCT/SE2014/050727
§ 371 (c)(1),
(2) Date: Dec. 17, 2015

(87) PCT Pub. No.: WO2014/204383
PCT Pub. Date: Dec. 24, 2014

(65) Prior Publication Data
US 2016/0152938 A1 Jun. 2, 2016

(30) Foreign Application Priority Data
Jun. 17, 2013 (SE) ...................... 1350731

(51) Int. Cl.
*C12M 1/34* (2006.01)
*C12M 1/00* (2006.01)
(Continued)

(52) U.S. Cl.
CPC ............ *C12M 41/12* (2013.01); *C12M 23/14* (2013.01); *C12M 23/48* (2013.01); *G01K 1/143* (2013.01); *G01K 1/16* (2013.01)

(58) Field of Classification Search
CPC ...... C12M 23/02; C12M 23/44; C12M 23/26; C12M 23/14; C12M 23/48; C12M 41/12;
(Continued)

(56) References Cited

U.S. PATENT DOCUMENTS 6,384,380 B1 * 5/2002 Faries, Jr. ............ A61G 12/001
219/385
9,948,952 B2 4/2018 Hwang et al.
(Continued)

FOREIGN PATENT DOCUMENTS

CN 201488829 U 5/2010
CN 102348967 A 2/2012
(Continued)

OTHER PUBLICATIONS

International Search Report and Written Opinion issued in connection with corresponding PCT application PCT/SE2014/050727 dated Sep. 16, 2014.
(Continued)

*Primary Examiner* — Nathan A Bowers
*Assistant Examiner* — Lydia Edwards
(74) *Attorney, Agent, or Firm* — Wood IP LLC

(57) ABSTRACT

A temperature sensor means comprising a thermally conducting layer arranged to face the surface to be measured, a thermally insulating layer attached to the thermally conducting layer on the opposite side to the surface to be measured, a temperature sensor provided between the thermally conducting layer and the thermally insulating layer and being completely surrounded on all its sides by either the thermally conducting or the thermally insulating layers.

11 Claims, 3 Drawing Sheets

(51) Int. Cl.
*C12M 3/00* (2006.01)
*G01K 1/14* (2006.01)
*G01K 1/16* (2006.01)

(58) Field of Classification Search
CPC ...... C12M 23/50; C12M 23/56; C12M 47/20; G01K 1/143; G01K 1/16; G01K 1/20; G01K 1/22; G01K 1/24
See application file for complete search history.

(56) References Cited

U.S. PATENT DOCUMENTS

| 2007/0215018 A1* | 9/2007 | Faries, Jr. ............... | A61B 50/10 109/23 |
|---|---|---|---|
| 2010/0327849 A1* | 12/2010 | Kamen ............... | A61M 1/1605 324/105 |
| 2012/0145587 A1 | 6/2012 | Yeo et al. | |
| 2012/0258441 A1 | 10/2012 | Gebauer | |
| 2013/0083326 A1 | 4/2013 | Clark et al. | |
| 2015/0204733 A1* | 7/2015 | Newell ................... | G01K 1/14 374/141 |
| 2016/0269711 A1 | 9/2016 | Hwang et al. | |

FOREIGN PATENT DOCUMENTS

| CN | 102656282 A | 9/2012 |
|---|---|---|
| EP | 0547750 A1 | 6/1993 |
| EP | 2015041 A1 | 1/2009 |
| EP | 2574891 A2 | 4/2013 |
| EP | 3110150 A1 | 12/2016 |
| JP | 2008232620 A | 10/2008 |
| JP | 2016519480 A | 6/2016 |
| WO | 2010/103436 A1 | 9/2010 |
| WO | 2014/204383 A1 | 12/2014 |

OTHER PUBLICATIONS

International Preliminary Report on Patentability Received for PCT Patent Application No. PCT/SE2014/050727, dated Dec. 22, 2015, 5 pages.
Extended European Search Report Received Received for European Patent Application No. 14814209.4, dated Feb. 17, 2017, 8 pages.
Office Action Received for Chinese Patent Application No. 201480045333.4, dated Jun. 2, 2017, 11 pages. (6 pages Office Action + 5 pages English Translation).

* cited by examiner

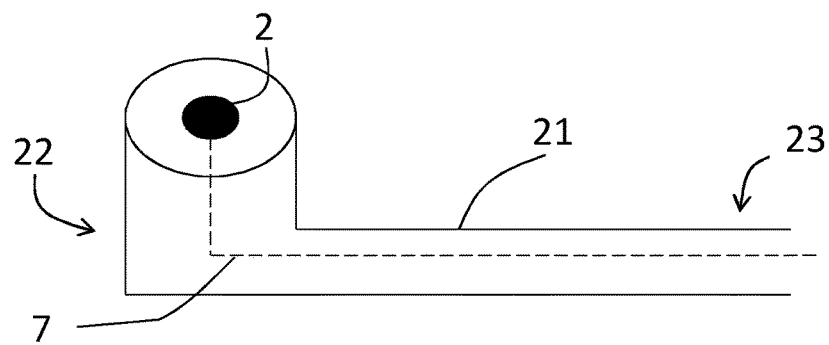
Figure 3
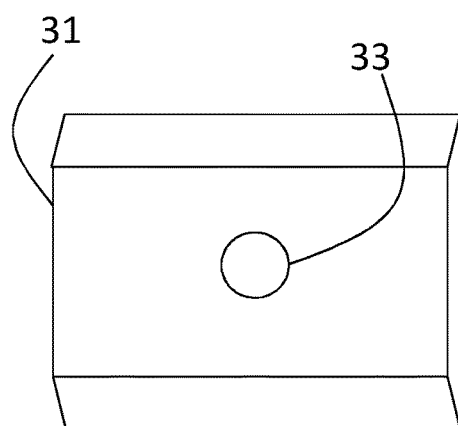 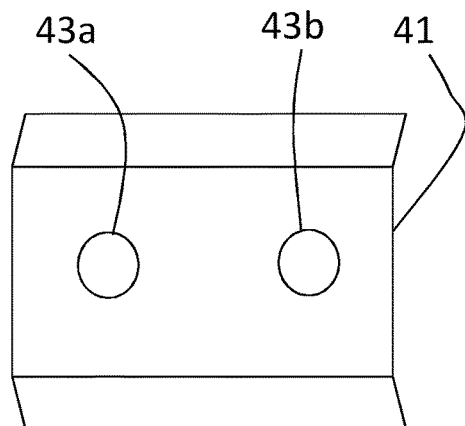
Figure 4a  Figure 4b

TEMPERATURE SENSOR MEANS AND A BIOREACTOR SYSTEM COMPRISING A TEMPERATURE SENSOR MEANS

TECHNICAL FIELD OF INVENTION

Embodiments of the present invention relates to a temperature sensor means and a bioreactor system comprising such a temperature sensor means.

BACKGROUND OF THE INVENTION

Measuring temperatures in bioreactors can be done invasively or noninvasively. Noninvasive measurements are preferred in many cases because the content of the bioreactor should not be contaminated. Temperature sensors provided outside the bioreactor have been used. A problem with such temperature sensors is that ambient temperature will affect the measured temperature.

SUMMARY OF THE INVENTION

The object of embodiments of the present invention is to provide reliable temperature measurements and to provide bioreactor systems that are easy to handle.

This is achieved in a temperature sensor means comprising a thermally conducting layer arranged to face the surface to be measured, a thermally insulating layer attached to the thermally conducting layer on the opposite side to the surface to be measured, a temperature sensor provided between the thermally conducting layer and the thermally insulating layer and being completely surrounded on all its sides by either the thermally conducting or the thermally insulating layers. Hereby a more reliable temperature measurement can be achieved because the influence from ambient temperature on the temperature measurement is decreased.

This is also achieved in a bioreactor system comprising a base station comprising a control system, a tray arranged to be provided on the base station and arranged to house a bioreactor bag, wherein the base station comprises at least one temperature sensor means, and in that the tray comprises at least one opening for receiving the temperature sensor means such that it will contact a surface of a bioreactor provided in the tray. Hereby a convenient bioreactor system is provided where the circulation in the bioreactor is not affected by the temperature sensor and where only the base station and not the tray holding the bioreactor need to be considered for calibration. Furthermore a bioreactor system providing reliable temperature measurements with very limited influence from ambient temperature is achieved.

BRIEF DESCRIPTION OF THE DRAWINGS

FIG. 3 shows schematically an arm comprising a temperature sensor means according to the invention, the arm being adapted to be used in a base station of a bioreactor system.

FIGS. 4A, 4B, and 4C show schematically trays adapted to be provided on a base station according to the invention and the trays being adapted to hold bioreactor bags.

DETAILED DESCRIPTION

Figure 1:
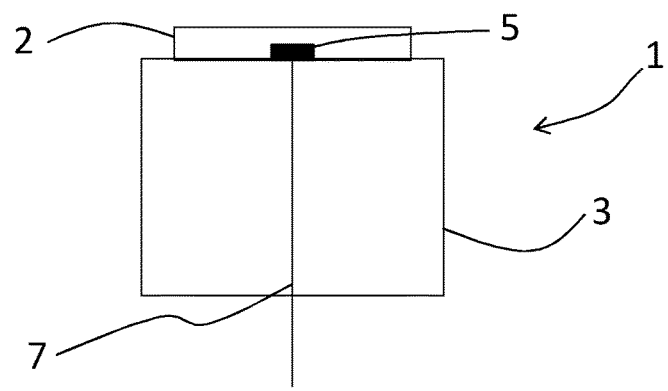
FIG. 1 shows schematically a temperature sensor means according to the invention.

FIG. 1 shows schematically a temperature sensor means 1 according to an embodiment of the present invention. The temperature sensor means comprises a thermally conducting layer 2 arranged to face the surface to be measured, a thermally insulating layer 3 attached to the thermally conducting layer 2 on the opposite side to the surface to be measured and a temperature sensor 5 provided between the thermally conducting layer 2 and the thermally insulating layer 3 and being completely surrounded on all its sides by either the thermally conducting or thermally insulating layers. The thermally conducting layer is a material with higher thermal conductivity than the thermally insulating layer. It could for example be a metal layer or a thermally conducting graphite or polymer layer. The temperature sensor 5 has a connection 7 through the thermally insulating layer to a control system. The thermally conducting layer 2 will improve the conductivity towards the surface to be measured and the thermally insulating layer 3 will decrease the influence from ambient temperature on the temperature sensor.

Figures 2A, 2B:
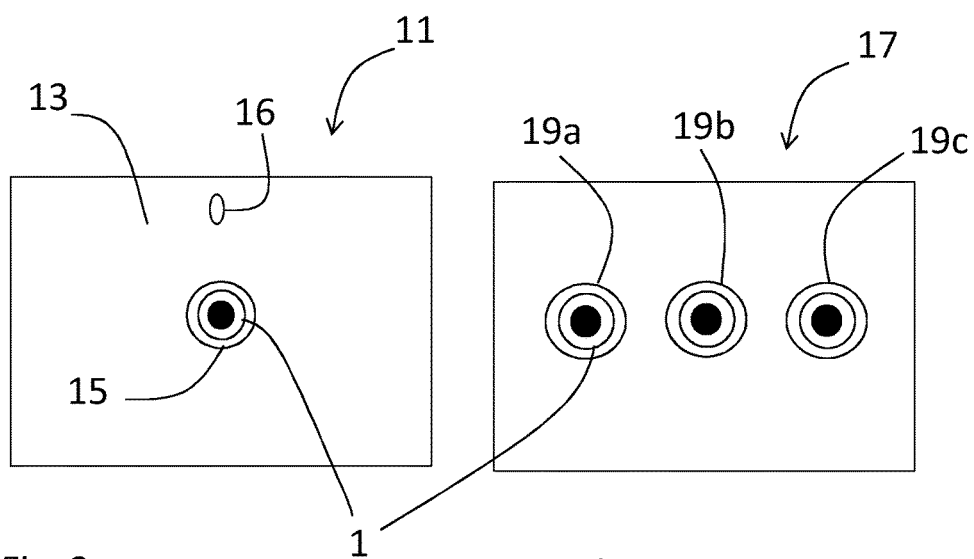
FIGS. 2A and 2B show schematically a base station of a bioreactor system according to two different embodiments of the invention comprising one or three temperature sensor means.

FIGS. 2A and 2B show schematically two examples of a base station of a bioreactor system according to a further aspect of an embodiment of the invention comprising one and three temperature sensor means as described in relation to FIG. 1 respectively. In FIG. 2A a base station 11 according to one embodiment of one aspect of the invention is schematically shown. The base station to a bioreactor system comprises of course many more details but they are omitted in the description of the embodiments of the present invention. In this embodiment the base station 11 comprises one temperature sensor means as described in relation to FIG. 1. Suitably the temperature sensor means 1 is provided on an arm 21 as shown in FIG. 3. The arm is provided inside the base station 11 under a base station upper surface 13. The arm 21 is provided such that the temperature sensor means can protrude up through an opening 15 in the base station upper surface 13. This can be achieved by providing the arm 21 as a lever. The temperature sensor means 1 is then provided onto one end 22 of the lever 21 and if something pushes down onto the other end 23 of the lever 21 the temperature sensor means 1 will move upwards and protrude through the opening 15 in the base station. Hereby the base station upper surface 13 also needs to be provided with another opening 16 for receiving a pushing means that will push the end of the lever opposite the temperature sensor means downwards. A tray adapted to hold a bioreactor and to be positioned onto the base station may comprise this one or more pushing means. Another possible design would be to provide the temperature sensor means 1 on a resilient arm 21 which protrudes up through the opening 15 in the base station upper surface 13 but easily is pushed back if something presses on the temperature sensor means 1 from above. In FIG. 3 an arm 21 with a temperature sensor means 1 is shown. This arm could be provided in the base station as described above either as a lever or as a resilient arm. In FIG. 3 a communication connection 7 from the temperature sensor through the thermally insulating layer 3 is shown.

In FIG. 2B a base station 17 according to another embodiment of the invention is schematically shown. In this embodiment three arms 21 comprising temperature sensor means are provided. Hereby also three openings 19a, 19b, 19c are provided in the base station upper surface.

Figure 4C:
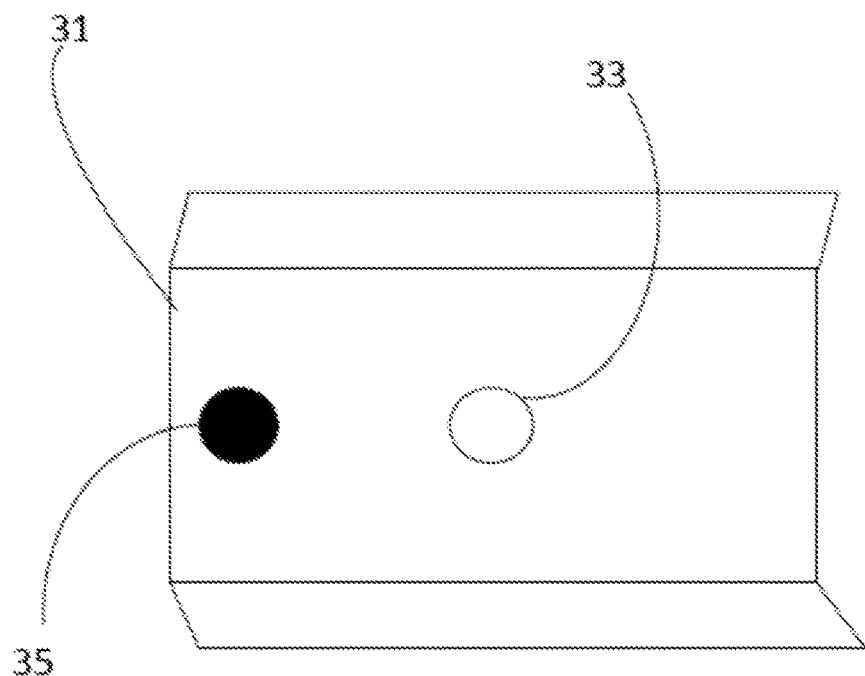

FIGS. 4A, 4B, and 4C show schematically trays adapted to be provided on a base station according to an embodiment of the present invention and the trays being adapted to hold bioreactor bags. The tray 31 of FIG. 4A can be used in either the base station 11 shown in FIG. 2A or the base station 17 shown in FIG. 2B. The tray 31 is adapted to hold a bioreactor bag and the tray comprises an opening 33 positioned to align with the opening 15 of the base station 11 of FIG. 2*a* and the middle opening 19*b* of the base station 17 of FIG. 2B. Suitably the opening 33 in the tray is somewhat larger than the temperature sensor means. Hereby the temperature measurements will be less effected by the heaters that often are provided in the trays. When the tray 31 of FIG. 4A is used together with the base station 17 of FIG. 2B the two other temperature sensor means provided through openings 19*a*, 19*c* will not be protruding up through the openings because the tray 31 does not comprise corresponding pushing means for these temperature sensor means arms (if the lever variant is used). If resilient arms instead are used the temperature sensor means provided through the openings 19*a*, 19*c* will be pushed downwards by the tray 31 and not be used.

The tray 41 of FIG. 4B can be used in the base station 17 shown in FIG. 2B. The tray 41 comprises two openings 43*a*, 43*b* to receive one temperature sensor means 1 each. In this embodiment the temperature sensor means 1 provided through the middle opening 19*b* of the base station 17 will not be used and the temperature sensor means provided through the opening 19*a* will protrude up through the opening 43*a* of the tray 41 and the temperature sensor means provided through the opening 19*c* will protrude up through the opening 43*b* of the tray 41. In this embodiment two bioreactor bags could be provided in the tray 41. The openings in the trays 33, 43*a*, 43*b* can in one embodiment be covered by a suitable thin film, for example a plastic film. This could be advantageous in order to keep any spillage in the tray. However, this is not necessary. Additionally, Tray 31 may comprise a pushing device 35, wherein the pushing device will push downward on one end of arm 21.

A control system of the bioreactor system comprises in one embodiment means for measuring the ambient temperature and means for compensating the bioreactor temperature measurement for different ambient temperatures.

In an embodiment of the present invention the temperature sensor or sensors are provided in the base station instead of in the different trays. Hereby the trays can be kept simple and without any need for calibration and electrical connections. In an embodiment, it is beneficial to have all of these functions in the base station.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A bioreactor system comprising
a base station comprising a control system,
a tray arranged to be provided on the base station and arranged to house a bioreactor bag,
   wherein said base station comprises at least one temperature sensor means, the system being characterised in that said temperature means includes:
   a thermally conducting layer arranged to face the bioreactor bag surface to be measured,
   a thermally insulating layer attached to the thermally conducting layer on the opposite side to the surface to be measured,
   a temperature sensor provided between the thermally conducting layer and the thermally insulating layer and being completely surrounded on all its sides by either the thermally conducting or the thermally insulating layers;
and further characterized in that said tray comprises a first opening for receiving said temperature sensor means such that in use the thermally conducting layer of the sensor will contact a surface of a bioreactor provided in the tray;
wherein the at least one temperature sensor means is provided on an arm;
wherein the arm is provided inside the base station and under a base station upper surface;
wherein the base station upper surface provides a second opening;
wherein the second opening is configured to receive a pushing device.

2. A bioreactor system according to claim 1, wherein the thermally conducting layer is a material having higher thermal conductivity than the thermally insulating layer.

3. A bioreactor system according to claim 1, wherein the thermally conducting layer is a metal or a thermally conducting graphite or polymer.

4. A bioreactor system according to claim 1 further comprising a communication connection provided through the thermally insulating layer from the temperature sensor.

5. A bioreactor system according to claim 1, wherein said temperature sensor device is provided in one end of the arm being a lever such that the pushing device provided on the tray will push downwards on the other end of the arm when the tray is provided in the base station and thereby the temperature sensor device will move upwards through the first opening in the tray such that the temperature sensor device will contact the bioreactor surface but not disturb the bioreactor surface.

6. A bioreactor system according to claim 1, wherein said base station comprises more than one temperature sensor device each temperature sensor device being mounted on a separate arm and different opening in different trays will decide which temperature sensor device to be contacting the bioreactor surface, whereby the other temperature sensor device will not be protruding through the openings in the tray.

7. A bioreactor system according to claim 1, wherein the control system comprises a device for compensating the temperature measurement for the ambient temperature.

8. A bioreactor system according to claim 2, wherein the thermally conducting layer is a metal or a thermally conducting graphite or polymer.

9. A bioreactor system according to claim 5, wherein said base station comprises more than one temperature sensor device, each temperature sensor device being mounted on a separate arm and different opening in different trays will decide which temperature sensor device to be contacting the bioreactor surface, whereby the other temperature sensor devices will not be protruding through the openings in the tray.

10. A bioreactor system according to claim 5, wherein the control system comprises a device for compensating the temperature measurement for the ambient temperature.

11. A bioreactor system according to claim 6, wherein the control system comprises a device for compensating the temperature measurement for the ambient temperature.

\* \* \* \* \*